United States Patent [19]
Baxter

[11] 4,455,212
[45] Jun. 19, 1984

[54] GEL ELECTRODE FOR EARLY DETECTION OF METAL FATIGUE

[75] Inventor: William J. Baxter, Bloomfield Hills, Mich.

[73] Assignee: General Motors Corporation, Detroit, Mich.

[21] Appl. No.: 353,163

[22] Filed: Mar. 1, 1982

[51] Int. Cl.³ ............................................... G01N 27/30
[52] U.S. Cl. .................................... 204/414; 204/1 T; 324/51; 324/52
[58] Field of Search .................. 204/1 T, 195 R, 414; 324/51, 52

[56] References Cited

U.S. PATENT DOCUMENTS

| | | | |
|---|---|---|---|
| 3,419,479 | 12/1968 | Klein | 204/1 T |
| 4,160,702 | 7/1979 | Baxter | 204/1 T |
| 4,190,501 | 2/1980 | Riggs | 204/1 T |

Primary Examiner—G. L. Kaplan
Attorney, Agent, or Firm—Douglas D. Fekete

[57] ABSTRACT

Early fatigue damage in aluminum is assessed by detection of microcracks in an anodized surface film using a hand-held electrode having a contact tip formed of a gel containing an iodide salt and starch. The gel tip is pressed against the anodized film and an electrical pulse is applied to pass current through the microcracks to oxidize iodide in the gel to form black iodine-starch complex. Thus, dark spots in the gel indicate the sites of fatigue-induced microcracks in the oxide and thus the extent of fatigue damage in the metal.

3 Claims, 4 Drawing Figures

| FATIGUE CYCLES | 0 | 300 | $10^3$ | $3\times10^3$ | $10^4$ | $3\times10^4$ |
|---|---|---|---|---|---|---|
| % LIFE | 0 | 0.2 | 0.7 | 2 | 7 | 20 |

GEL ELECTRODE FOR EARLY DETECTION OF METAL FATIGUE

BACKGROUND OF THE INVENTION

This invention relates to early assessment of fatigue damage in an aluminum structural member by detecting fatigue-induced microcracks in a surface oxide film. More particularly, this invention relates to a gel electrode that is adapted to be pressed against a selected region of an oxidized metal surface and developed by an electrical pulse to form a visible display showing the location of fatigue-induced microcracks in the region.

Cyclic, low stress loading of an aluminum structural member produces fatigue that creates cracks in the metal and ultimately leads to catastrophic failure of the member. In the early stages of fatigue, prior even to the formation of significant cracks in the aluminum, microcracks form in the more brittle oxide film that covers the aluminum surface. It has been found that the severity of oxide cracking is related to the extent of fatigue damage in the underlying aluminum and provides a basis for predicting the useful lifetime of the structural member. Prior methods for detecting the microcracks, such as a reanodization method described in U.S. Pat. No. 4,160,702, are useful for laboratory tests, but have not been suitable for assessing damage to a structural part in the field, particularly because they require removal of the part. In addition, prior methods provide general readings over a part surface, but are not readily adaptable for selectively testing regions of the surface or for pinpointing the sites of the microcracks.

Therefore, it is an object of this invention to provide a simpler method for the early assessment of fatigue damage in a selected region of a structural member formed of a metal such as aluminum by the detection of fatigue-induced microcracks in a surface oxide film, which method is quickly carried out on the member to provide a visual display showing the number, location and size of microcracks in the region. Optionally, the method also provides an electrical measure of the severity of microcracking. The method is suitable for detecting microcracks without damage to the member or requiring removal from its structural environment and provides an accurate basis for predicting the useful life of the member prior to failure.

It is also an object of this invention to provide an electrical probe, and a method employing the probe, for mapping a selected region of an oxidized metal surface to visually display the sites of fatigue-induced microcracks. The probe comprises a pliable, nonadherent tip that is adapted to be placed in contact with the region and electrically developed to show the microcracks in a few seconds or even substantially faster. The probe is portable for readily testing an accessible surface of a structural member while in its working environment. Optionally, the probe is adapted to provide an electrical measure of the extent of oxide microcracking in addition to the visual display.

SUMMARY OF THE INVENTION

In a preferred embodiment, an aluminum part is anodized prior to placing it in a service environment wherein it is subjected to cyclic stresses of the type that produce fatigue damage in the aluminum. The anodization forms an electrically insulative, aluminum oxide film on the aluminum surface that is thicker and more resistive than natural oxide. When the part is subsequently placed in service, fatigue damage to the aluminum creates microcracks in the thick oxide film that exposes the underlying metal. The exposed metal reacts with air and thus becomes covered by a natural oxide.

The fatigue-induced microcracks are detected with the aid of a hand-held electrode having a round contact tip formed of a self-skinning, white, pliant gel containing an iodide salt and starch. Without necessarily removing the part from service, the gel tip is gently pressed against a selected region of the oxide surface. An electrical pulse is applied between the aluminum part, which is positively biased, and the gel. The pulse causes current to flow through the thinner, natural oxide at the microcracks but not through the thicker oxide. In the gel adjacent the microcracks, the current oxidizes iodide into a state that forms a dark-colored complex with starch. Visible dark spots develop in the gel after only a short time, ranging between a fraction of a second up to, at most, a few seconds, depending upon the applied voltage. The electrode is then removed and the gel tip visibly examined for dark spots that reveal the sites of fatigue-induced microcracks. The location, number and size of the spots indicate the extent of oxide cracking and thus fatigue damage in the underlying metal.

Prefatigue anodization has essentially no effect upon the strength or performance of the part in service. Anodization covers scratches or other imperfections in the metal surface so that only subsequent fatigue-induced microcracks are detected by the electrode. The method of this invention is particularly well suited for assessing fatigue damage produced while the part is exposed to air, as is typically found. In addition to providing a visible record, the pulse current may be readily measured and is also directly related to the extent of fatigue-induced oxide cracking. Both visual examination and current measurement provide basis for predicting the life of the part prior to fatigue failure.

DETAILED DESCRIPTION OF THE INVENTION

Figure 1:
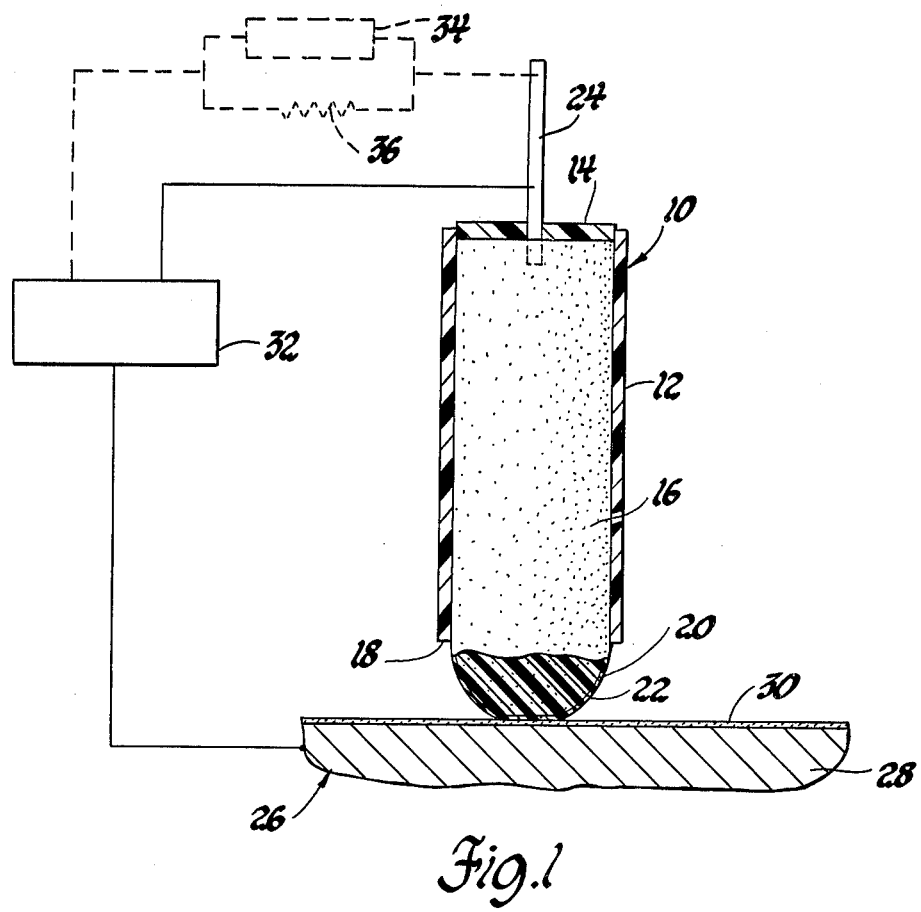
FIG. 1 is a cross sectional view of a gel electrode in contact with an anodized aluminum surface for detecting fatigue damage in accordance with this invention.

In a preferred embodiment, evidence of early fatigue damage to an aluminum part is obtained using electrode 10 in FIG. 1. Electrode 10 is sized to be conveniently hand held and comprises a cylindrical polymeric tube 12 having a cross sectional diameter of about 6 millimeters. One end of tube 12 is sealed by the silicone membrane 14. Tube 12 is substantially filled with a hydrous agar gel 16. Gel 16 is prepared by dissolving about 3.2 grams potassium iodide, KI; about 1.9 grams borax and about 3 grams corn starch in 100 milliliters warm water. To the warm solution is added 0.7 grams agar powder.

The viscous product liquid is poured into tube 12 through open end 18 and cooled to form a white, semitransparent gel. Some small air bubbles may be trapped in the viscous liquid after pouring, but do not normally interfere with electrode operation. Tube 12 is overfilled slightly so that a convex meniscus forms as the result of surface tension and produces a round electrode tip 20. Dehydration of the gel surface at tip 20 causes a skin 22 to form after about five minutes. Gel 16 with skin 22 is sufficiently pliable to permit good contact between tip 20 and an oxidized aluminum surface, but does not adhere to the surface. An aluminum wire 24 embedded into gel 16 through membrane 14 provides an electrical lead to the gel.

A part whose fatigue life is of interest is indicated generally at 26 in FIG. 1 and is formed of aluminum 28. Prior to subjecting part 26 to fatigue conditions, the part is pretreated by anodizing aluminum 28 to form on the surface a thick, integral oxide film 30. Part 26 is cleaned with an aqueous chromic acid-sulfuric acid solution and immersed in a room temperature, three percent by weight aqueous tartaric acid solution having a pH of about 5, adjusted using ammonium hydroxide. An electrical potential is applied between part 26 and a spaced aluminum cathode to anodically bias the part. The potential is slowly increased to about 10 volts while maintaining a constant current density of about 10 milliamperes per square centimeter and then maintained constant until the current falls below $1 \times 10^{-3}$ milliamperes per square centimeter. Under these conditions the aluminum surface oxidizes to form alumina that builds up on the surface to form film 30 about 14 nanometers thick. In contrast, an oxide formed naturally by reacting with oxygen in air is about 3 to 4 nanometers thick.

The anodized part is then subjected to conditions including periodic stressful loading and unloading that produces fatigue in aluminum 28. In the very early stages of fatiguing, prior to any readily detectable damage to aluminum 28 itself, the fatigue creates microcracks in the more brittle oxide film 30. The microcracks expose fresh metal to air, whereupon a natural oxide forms over the exposed metal.

Figure 2:
FIG. 2 comprises a series of photographs showing tips of gel electrodes employed to detect microcracks in anodic oxides on aluminum bars subjected to specified numbers of fatigue test cycles.

When it is desired to assess the fatigue damage to aluminum 28, tip 20 of electrode 10 is manually pressed against anodized surface 30 of part 26, as shown in FIG. 1, whereupon skin 22 deforms to produce intimate contact. The electrode wire 24 and aluminum 28 are then connected to the negative and positive poles, respectively, of a direct current electrical power source 32 and an electrical pulse of about 5 volts is applied for about 5 seconds. The pulse does not produce significant current through the thicker, anodic oxide 30, but does cause electrons to flow from gel skin 22 into aluminum 28 through the thinner natural oxide formed at the fatigue-induced microcracks. This selective current flow is attributed to differences between the electrical resistance of the anodic oxide and the natural oxide resulting principally from the difference in thickness. This current oxidizes iodide ions in the gel skin to form iodine ions, $I_3^-$, that, in turn, form a black complex with the starch. After the pulse, electrode 10 is removed from part 26 and tip 20 is examined for visible dark spots, such as shown in FIG. 2. The spots result from the accumulation of iodine-starch complex and thus correspond to sites of microcracks in the oxide. It is noted that the tips in FIG. 2 were developed substantially more than necessary so that the spots would be clearly seen in the photograph.

The density of spots printed onto the electrode tip 20 indicates the degree of fatigue damage in the aluminum part. The gel tips shown in FIG. 2 were printed from anodized 6061-T6 aluminum alloy bars subjected to fatigue testing which included cyclic bending. The average life before breaking into two pieces, referred to as catastrophic failure, was about 140,000 cycles. The bars for FIG. 2 were subjected to substantially fewer cycles, corresponding to only a relatively small fraction of the expected life. As can be seen, the density of spots is directly related to the number of fatigue cycles.

Figure 3:
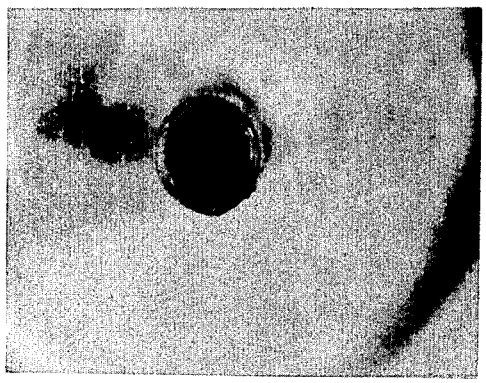
FIG. 3 is a photograph showing an electrode gel tip produced by a microscopic fatigue crack in the metal of an aluminum test bar.

Oxide microcracks that result from early fatigue damage are different from fatigue cracks formed in the aluminum itself. Fatigue cracks in the metal also form cracks in the anodized film and may be detected by the electrode and method of this invention. FIG. 3 shows a fatigue crack formed in an anodized 6061-T6 aluminum strip subjected to about 80,000 bending cycles. The gel pattern was developed by applying a pulse of 10 volts for about 50 milliseconds. The higher voltage and shorter time optimized resolution of the fatigue crack. The tip also comprises numerous spots produced by microcracks in the oxide, which are visible, particularly with the aid of a magnifier, but did not reproduce well in the photograph.

Metal cracks such as printed in FIG. 3, while still microscopic, are obviously larger than early formed oxide cracks such as printed in FIG. 2 and represent substantial metal damage, indicating that the metal is dangerously near catastrophic failure. A principal advantage of this invention is that, by detecting oxide microcracks, it allows fatigue to be assessed in its early stages, prior to crack formation in the metal.

Figure 4:
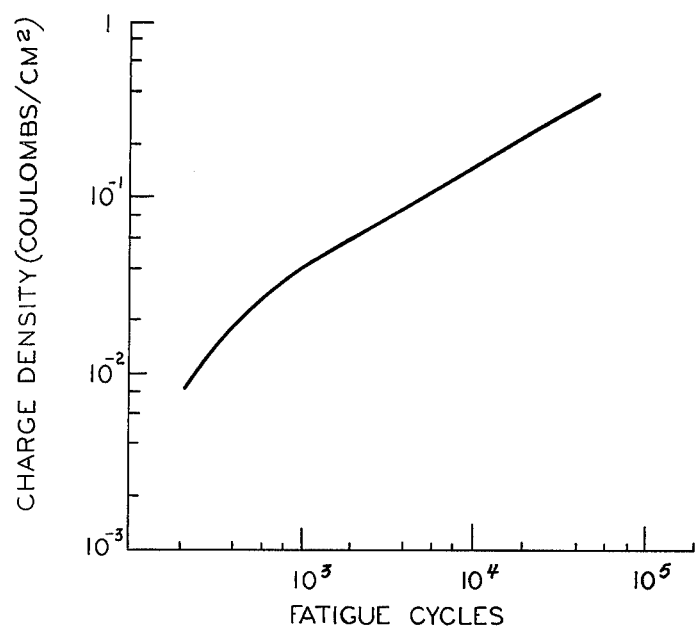
FIG. 4 is a graph depicting charge density of an electrical pulse applied between anodized aluminum and a gel electrode as a function of fatigue test cycles.

The electrode and method of this invention are readily adapted to provide an electrical measurement in addition to a visible print. Referring again to FIG. 1, dashed lines depict an alternate circuit for measuring charge flow resulting from the applied pulse. An oscilloscope 34 and a 100 ohm resistor 36 are connected in parallel between power source 32 and electrode lead 24. The oscilloscope trace is adjusted so that the sweep time is greater than the pulse duration and the amplitude measures current flow during the pulse. Because film 30 is basically insulative, the metal-film-electrode forms a capacitor and there is initially a current spike resulting from capacitive charging. For the described embodiment, the capacitance is about 0.1 microfarad, and on the order of $10^{-6}$ coulomb is required for charging. Thereafter, the current drops and then rises to show current flow through the microcracks. The integral of the current, which is the area under the trace, is a measure of the total charge flow. To correct for variations in the area of gel contact, the measured charge is divided by the area, typically about 0.13 square centimeters, to calculate a charge density. FIG. 4 shows charge density as a function of test cycles for aluminum alloy test bars fatigued in the manner described for FIG. 2. As can be seen, the charge density is directly related to the number of fatigue cycles. A background density of about $7 \times 10^{-4}$ coulombs per square centimeter is attributed to nonfatigue defects in the anodized film.

Although metal fatigue produces microcracks even in natural oxides, the method of this invention preferably employs an oxide film that is sufficiently thicker to provide a detectable difference between the resistance of the film and the natural oxide, thereby allowing the part to be exposed to air when cracking occurs. Anodizing is preferred for growing the initial oxide film on aluminum, but suitable oxides are also grown by other methods, such as heating in air or plasma oxidation. Oxides greater than about 100 nanometers tend to crack independent from fatigue and thus are not as useful. In general, oxide films between 10 to about 20 nanometers thick are preferred. The method of this invention is also suitable for use with metals other than aluminum and aluminum alloys that may be pretreated to form an adherent oxide film thicker than natural oxide, for example, titanium or tantalum.

The sensitivity and spatial resolution of the electrode are determined by the magnitude and duration of the applied potential. In general, higher voltages and shorter times provide better spatial resolution, but reduce sensitivity. Although a 5 volt pulse is applied in the described embodiment, a 10 volt pulse is preferred because it substantially reduces the exposure time. For a 10 volt pulse, 100 milliseconds produce an image that is readily visible, but overexposed; whereas one millisecond produces a barely visible image having excellent spatial resolution. About 10 milliseconds is preferred.

While this invention has been described in terms of a particular embodiment thereof, it is not intended to be limited to the above description but rather only to the extent set forth in the claims that follow.

What is claimed is:

1. An electrode for detecting microcracks in a selected region of an oxide film overlying a metal substrate and for developing a visible record indicating the microcracks in said region, said electrode comprising
    a housing having an opening,
    a pliable, electrically conductive gel body comprising iodide ions and starch in concentrations suitable for forming visible, dark color in response to oxidation of iodide in the body, said gel body being contained in the housing and protruding from the opening so as to form a round contact that is adapted to be brought into intimate contact with an oxide film surface and removed, and
    means for connecting the gel to one pole of an electrical power source for cathodically biasing the contact.

2. An electrode for detecting fatigue-induced microcracks in a selected region of an oxide film overlying a metal substrate and for developing a visible record indicating sites of microcracks in said region, said electrode comprising
    a tubular housing having an open end,
    an electrically conductive body formed of a hydrous agar gel containing iodide ions and starch, said iodide ions and starch being suitable for forming a dark color as a result of oxidation of said iodide and being present in amounts effective to produce visible concentrations of the dark color, said gel body being contained in said housing and protruding from the open end so as to form a convex tip that is adapted to be pressed against an oxide film surface, said gel tip having a dehydrated skin and being sufficiently pliable for intimate contact when pressed against an oxide film surface, but nonadherent for removal intact from the film, and
    means for connecting the gel to one pole of an electrical power source for cathodically biasing the tip, whereby current flow in the tip is indicated by the development of visible, dark color.

3. An electrode for detecting microcracks in an oxide film overlying a metal substrate and for developing a visible record indicating the microcracks, said electrode comprising
    a housing having an opening, and
    a pliable, electrically conductive gel body comprising iodide ions and starch, said body being contained in the housing and protruding from the opening to form an electrical contact.

* * * * *